United States Patent [19]
Sirdesai et al.

[11] Patent Number: 6,100,097
[45] Date of Patent: Aug. 8, 2000

[54] METHOD AND APPARATUS FOR DETECTING METHACRYLATE IN A LIQUID MONOMER

[75] Inventors: Sunil J. Sirdesai, Irvine; George Schaeffer, Beverly Hills, both of Calif.

[73] Assignee: OPI Products, Inc., North Hollywood, Calif.

[21] Appl. No.: 09/059,027

[22] Filed: Apr. 13, 1998

[51] Int. Cl.[7] .................................................. G01N 33/00
[52] U.S. Cl. ............................................ 436/129; 436/166
[58] Field of Search ................................ 436/128–129, 436/85, 166

[56] References Cited

U.S. PATENT DOCUMENTS 3,301,912  1/1967  Hwang et al. .

FOREIGN PATENT DOCUMENTS

| 46-9136 | 3/1971 | Japan . |
| 8-101127 | 4/1996 | Japan . |
| 1508331 | 4/1978 | United Kingdom . |
| 1528418 | 5/1978 | United Kingdom . |

*Primary Examiner*—Arlen Soderquist
*Attorney, Agent, or Firm*—Leonard Tachner

[57] ABSTRACT

A method for identifying methyl methacrylate (MMA) in the liquid part of a liquid/powder system used to form artificial finger nails and toenails. The chemistry used to identify MMA in liquid monomers provides an accurate and inexpensive way to monitor the use of MMA in liquid monomers in violation of a ban of MMA by the Food and Drug Administration (FDA) for purposes of creating artificial finger nails and toenails.

4 Claims, 1 Drawing Sheet where R1 = H, -CH3, -CH-(CH3)2, n-C3H7, n-C2H5 where R1 = H, -CH3, -CH-(CH3)2, n-C3H7, n-C2H5

METHOD AND APPARATUS FOR DETECTING METHACRYLATE IN A LIQUID MONOMER

BACKGROUND OF THE INVENTION

1. Field of the Invention

This invention relates to a portable kit and a method to identify methyl methacrylate (MMA) in liquid monomers by a calorimetric method.

2. Background Art

There exists a dire need in the nail care industry to identify MMA in the liquid monomer used to form artificial nails. The presence of MMA in liquid monomers to form artificial fingernails has been banned by Food and Drugs Administration (FDA) because of its deleterious properties. To date, there has not been a portable method to determine MMA or any other monomer at field sites. Chromatography techniques like gas chromatography, liquid chromatography, gas chromatography-mass spectroscopy and liquid chromatography-mass spectroscopy, are the only methods to detect monomers. These instruments of analysis are bulky and are definitely not portable to be carried to field sites for spot analysis. The lack of portable methods to determine MMA has hampered the policing activity of health regulators. These regulators have to ship the liquid samples suspected to contain MMA to commercial analytical laboratories for analysis. Test results for these liquid samples are obtained in about a week. This process, besides being expensive, is time consuming and policing of the nail care salons becomes ineffective.

There is thus a need for a method, which besides being portable and inexpensive, can identify MMA in liquid monomers within minutes. Armed with a portable kit, the health regulators would be far more effective in rooting out corrupt salons that continue to use MMA in preparing artificial nails.

SUMMARY OF THE INVENTION

This invention comprises a kit which health regulators can carry to nail care salons to identify MMA, if it is present, in the liquid part of the liquid/powder system, within a period of about a minute or so.

The invention utilizes the reaction of methacrylate with palladium-molybdate to yield a methacrylate-palladium molybdate complex. Because palladium has tendency to form a coordinate bond with olefins, the structure of the complex is postulated to be that shown in FIG. 1. Applicants discovered that only methyl methacrylate-palladium molybdate complex is blue in color while the complexes of other methacrylates are a green or yellow color. This color is leached out with polar solvents in order to facilitate the interpretation of the color of the solid complex.

Applicants also discovered that using palladium-molybdate complex that is adsorbed on silica or alumina instead of neat palladium-molybdate complex in the test, considerably shortens the procedure.

OBJECTS OF THE INVENTION

It is therefore a principal object of the present invention to provide a method and apparatus for detecting methyl methacrylate in the liquid portion of liquid/powder systems for forming artificial nails and distinguishing methyl methacrylate from other methacrylates.

It is another object of the invention to provide a portable kit comprising chemicals and devices to enable a rapid method for detecting methyl methacrylate in the liquid portion of liquid/powder systems used by salons to form artificial nails.

It is still another object of the invention to provide a method for policing the FDA ban on the use of methyl methacrylate by nail salons, the method permitting a color-based portable test which can be completed at each salon in only minutes.

It is still an additional object of the invention to provide a method and apparatus to facilitate enforcement of a federal ban on the use of methyl methacrylates in salons for forming artificial nails by detecting in the field, quickly and inexpensively, such methyl methacrylates and distinguishing from other methacrylates by means of a difference in color.

BRIEF DESCRIPTION OF THE DRAWINGS

The aforementioned objects and advantages of the present invention, as well as additional objects and advantages thereof, will be more fully understood hereinafter as a result of a detailed description of a preferred embodiment when taken in conjunction with the following drawing in which.

DETAILED DESCRIPTION OF THE PREFERRED EMBODIMENTS

Figure 1:
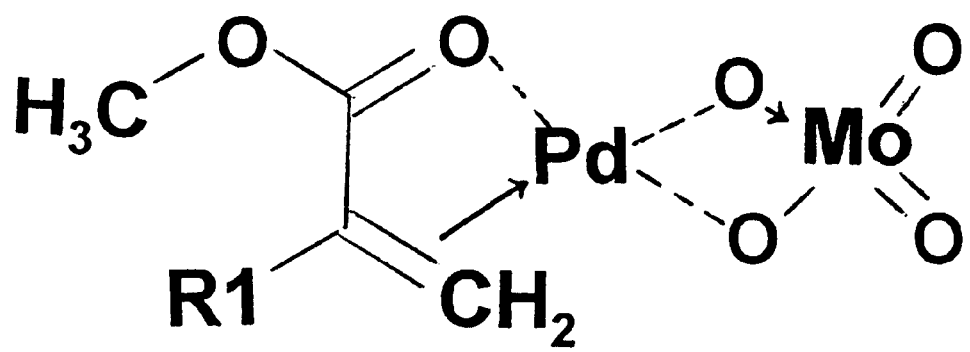
FIG. 1 is a postulated chemical structure diagram of methyl methacrylate-palladium molybdate complex that results from the method of the invention hereof.

This invention comprises both a method for detecting MMA and a combination of compositions forming a portable kit for carrying out the method. There are two variations of the portable kit. Depending on the kit, there is a slight change in test procedures.

FIRST EMBODIMENT

Portable Kit A consists of:

(1) Palladium molybdate powder
(2) Polar solvent
(3) Stirrer
(4) Small polystyrene cups or glass vials
(5) Droppers
(6) Filter paper Palladium-molybdate powder is supplied in a pre-weighed pouch either in inert atmosphere or in vacuum.

A method for identifying MMA in the liquid part of liquid/powder system for forming an artificial nail is as follows:

A small portion of liquid monomer (0.5 ml. to 5 ml.) is dispensed in the polystyrene cup or glass vial with the help of dropper. The pouch of palladium-molybdate powder (0.05 g. to 0.2 g.) is punctured and added to the liquid monomer in the cup or vial. This powder is then stirred for a few seconds to let the reaction go to completion. Residual monomer is filtered and the residue on the filter paper is transferred back into the cup or vial. Then a polar solvent (1 ml. to 5 ml.) is added to the residue to leach out the colored methacrylate-palladium molybdate complex. The color of the solvent is observed. If the color is green or yellow, the monomer does not contain MMA. If the color of the solvent is blue, the liquid contains MMA monomer. Methyl methacrylate-palladium molybdate complex is the only methacrylate complex that is blue in color.

SECOND EMBODIMENT

Portable Kit B consists of:

(1) Palladium molybdate powder adsorbed on silica or alumina (2) Polar Solvent (3) Stirrer (4) Small polystyrene cups or glass vials (5) Droppers Palladium-molybdate powder is supplied in a pre-weighed pouch either in inert atmosphere or in vacuum.

Another embodiment of the method for identifying MMA in the liquid part of liquid/powder system for forming an artificial nail is as follows:

A small portion of liquid monomer (0.5 ml. to 5 ml.) is dispensed in the polystyrene cup or glass vial with the help of dropper. The pouch of Palladium-molybdate powder (0.05 g. to 0.2 g.) is punctured and added to the liquid monomer in the cup or vial. This powder is then stirred for few seconds to let the reaction go to completion. Residual monomer is decanted and a polar solvent (1 ml. to 5 ml.) is then added to leach out the Methacrylate-palladium molybdate complex adsorbed on silica or alumina that is left behind in the cup or vial. With this kit embodiment only decantation is needed instead of a cumbersome and time consuming filtration process to remove the residual monomer. The color of the solvent is observed. If the color is green or yellow, the monomer does not contain MMA. If the color of the solvent is blue, the liquid contains banned MMA monomer.

In both embodiments of the invention the polar solvent is any one or more of the following: isopropyl alcohol, acetone, methyl ethyl ketone, methyl isobutyl ketone, methyl isoamyl ketone, 2-Pentanone and hexanone. There may be other suitable solvents for use in the process of the invention.

Having thus described preferred embodiments of the apparatus and method of the invention, it being understood that the disclosed embodiments are only illustrative and not necessarily limiting of scope, what we claim is:

1. A method of identifying methyl methacrylate and distinguishing from other methacrylates in a liquid monomer; the method comprising the following steps:

dispensing about 0.5 to 5 ml. of said liquid monomer into a container;

providing about 0.05 to 0.2 grams of palladium-molybdate powder and adding said powder to said container and stirring the resulting mixture;

providing filter paper to filter residual monomer, leaving a residue on the filter paper;

adding a polar solvent in an amount of about 1 to 5 ml. to said residue and observing the resulting color whereby a blue color indicates the presence of methyl methacrylate in said liquid monomer and any other color indicates the absence of methyl methacrylate.

2. The method recited in claim 1 wherein said polar solvent is taken from the group consisting of isopropyl alcohol, acetone, methyl ethyl ketone, methyl isobutyl ketone, methyl isoamyl ketone, 2-pentanone and hexanone.

3. A method of identifying methyl methacrylate and distinguishing from other methacrylates in a liquid monomer; the method comprising the following steps:

dispensing about 0.5 to 5.0 ml. of said liquid monomer into a container;

providing about 0.5 to 0.2 grams of palladium-molybdate powder adsorbed on at least one of silica and alumina and adding said adsorbed powder to said container and stirring the resulting mixture;

decanting residual liquid monomer, adding a polar solvent in an amount of about 1 to 5 ml. to the remaining portion of said mixture and observing the resulting color whereby blue indicates the presence of methyl methacrylate in said liquid monomer and any other color indicates the absence of methyl methacrylate.

4. The method recited in claim 3 wherein said polar solvent is taken from the group consisting of isopropyl alcohol, acetone, methyl ethyl ketone, methyl isobutyl ketone, methyl isoamyl ketone, 2-pentanone and hexanone.

* * * * *